United States Patent
Souppe et al.

(10) Patent No.: US 6,361,808 B1
(45) Date of Patent: Mar. 26, 2002

(54) PROCESS FOR THE PRODUCTION OF ALCOHOLIC BEVERAGES USING MALTSEED

(75) Inventors: Jerome Souppe, Wasquehal (FR); Robert Franciscus Beudeker, Den Hoorn (NL)

(73) Assignees: Mogen International NV, Leiden; Gist-Brocades N.V., Delft, both of (NL)

(*) Notice: Subject to any disclaimer, the term of this patent is extended or adjusted under 35 U.S.C. 154(b) by 0 days.

(21) Appl. No.: 09/230,590

(22) PCT Filed: Jul. 23, 1997

(86) PCT No.: PCT/EP97/04016

§ 371 Date: Apr. 28, 1999

§ 102(e) Date: Apr. 28, 1999

(87) PCT Pub. No.: WO98/05788

PCT Pub. Date: Feb. 12, 1998

(30) Foreign Application Priority Data

Aug. 5, 1996 (EP) ............................................. 96202195

(51) Int. Cl.⁷ .............................................. C12C 11/00
(52) U.S. Cl. ........................................................ 426/29
(58) Field of Search ......................... 426/592, 28, 16, 426/12, 11, 29; 435/185, 93

(56) References Cited

U.S. PATENT DOCUMENTS

| | | |
|---|---|---|
| 3,716,365 A | 2/1973 | Walmsley et al. .............. 99/51 |
| 5,487,989 A | 1/1996 | Fowker et al. ............... 435/165 |
| 5,866,526 A * | 2/1999 | Olsen et al. ................. 510/392 |
| 6,265,000 B1 * | 7/2001 | Shimamura et al. .......... 426/16 |

FOREIGN PATENT DOCUMENTS

| | | |
|---|---|---|
| DE | 2227976 | 1/1974 |
| DE | 3207676 | 10/1982 |
| DE | 275704 | 1/1990 |
| EP | 0227159 | 7/1987 |
| EP | 0449376 | 10/1991 |
| EP | 0479359 | 4/1992 |
| GB | 1442402 | 7/1976 |
| WO | 9009436 | 8/1990 |
| WO | 9606935 | 3/1996 |
| WO | 9629416 | 9/1996 |
| WO | 9742301 | 11/1997 |

OTHER PUBLICATIONS

Jensen L.G. et al. "Transgenic barley expressing a protein–engineered, thermostable (1,3–1,4)–beta–glucanase during germination" *Proc. Natl. Acad. Sci. USA*, vol. 93 (Apr. 1996), pp. 3487–3491.

Pen, J. et al. "Production of Active *Bacillus Licheniformis*-Alpha–Amylase in Tobacco and Its Application in Starch Liquefaction" *Biotechnology*, vol. 10 (Mar. 1992), pp. 292–296.

Herbers, K. et al. "A thermostable Xylanase from Clostridium Therocellum Expressed at High Levels in the Apoplast of Transgenic Tobacco Has No Detrimental Effects and Is Easily Purified." *Bio/Technology*, vol. 13 (Jan. 1995), pp. 63–66.

Vickers, J.E. et al. "Assessment of *Bacillus lichenformis* α–Amylase as a candidate Enzyme for Genetic Engineering of Malting Barley" *J. Inst. Brew.*, vol. 102 (Mar.–Apr., 1996), pp. 75–78.

Vickers, J.E. et al. "Thermostable Alpha–Amylase Cloned for Genetic Transformation of Barley" *Aust. Soc. Biochem Mol. Biol.*, vol. 26, Col–5–4, Jan. 1994.

McElroy, D. et al. "What's Brewing in Barley Biotechnology?" *Bio/Technology*, vol. 13 (Mar. 1995) pp. 245–249.

* cited by examiner

*Primary Examiner*—Keith Hendricks
(74) *Attorney, Agent, or Firm*—Ladas & Parry

(57) ABSTRACT

The invention relates to a process for the production of alcoholic beverages such as beer or whiskey with a mixture of enzymes comprising an endo-β(1,4)-xylanase, an arabinofuranosidase, an alpha-amylase, an endo-protease and a β-(1,3, 1,4)-glucanase, and optionally, a saccharifying amylase and/or an exopeptidase. Preferable are mixtures in which the enzymes which are necessary in the brewing process are provided by transgenic seeds. Only a minor amount of malt may be necessary for flavor and color.

9 Claims, 2 Drawing Sheets

PROCESS FOR THE PRODUCTION OF ALCOHOLIC BEVERAGES USING MALTSEED

This application is a 371 of PCT/EP97/04016, filed Jul. 23, 1997.

FIELD OF THE INVENTION

The present invention relates to a process for the production of alcoholic beverages, especially beer and whiskey.

BACKGROUND OF THE INVENTION

Alcoholic beverages such as beer can be manufactured from malted and/or unmalted barley grains. Malt, in addition to yeast, contributes to flavor and color of the beer, Furthermore, malt functions as a source of fermentable sugar and enzymes. Whether malt is used in the brewing process depends on the type of beer and on the country where the beer is produced. In African countries, for example, there is no tradition of using malt.

The general process of malting and brewing is recently described by R. C. Hoseney (Cereal Foods World, 39(9), 675–679, 1994). Malting is the process of controlled germination followed by controlled drying of the barley grain. Grain is converted into malt by successive steps of steeping, germination, growth and drying (kilning). In this respect, the germination step is important to obtain expression of a series of enzymes which enables modification of the endosperm. This modification produces fermentable carbohydrates.

The subsequent drying/heating step of the malting process produces flavor and color due to non-enzymatic browning (Maillard) reactions.

The process of malting is a very complicated and costly part of the beer production process. Several disadvantages of the malting process can be mentioned:

- the enzyme level of malt is variable which leads to unpredictable results,
- not every enzyme activity which is desirable is formed or is formed in sufficient amounts during germination, which makes enzyme supplementation necessary,
- conditions which flavor high flavor and color may be deleterious for enzyme activity of the malt,
- the process is expensive,
- 10–20% loss in weight occurs during germination, due to respiration and growth of rootlets (which are removed during cleaning of the malt),
- it is not possible to produce malt at any place which is desirable, because of unflavorable climate conditions,
- the use of malt can lead to colloidal instability because of solubilization of protein by protease present in the malt,
- formation of biogenic amines can occur (J. Food Science 59(5), 1104–1107, 1994), which may lead to e.g. histaminic intoxication.

Traditionally, malt was the only source of fermentable carbohydrates and enzymes, and in many countries it still is. However, to date more and more beers are produced using other sources of carbohydrates than malt and/or barley, i.e. virtually any starch source or liquefied/degraded starch, the so-called adjuncts. Since malt not only functions as a source of fermentable carbohydrate, but also as a source of enzymes, alternative enzyme sources have to be provided upon substitution of more than approximately 50% malt with unmalted barley and/or with adjuncts. Moreover, malt gives the beer flavor and color.

In the production of malt there is a trade-off between flavor and color and enzyme activity. A malt providing high flavor and dark color can only be produced after more extensive drying at relatively high temperatures. These are conditions which are deleterious for the activity of an enzyme. Thus the supplementation of enzymes from an exogenous source is necessary from several points of view. In that respect, the use of microbial enzymes has been common practice for some time. For example, for brewing beer grains and/or malted grains are liquefied and saccharified in order to yield fermentable sugars. Liquefaction steps may be improved by the use of thermostable alpha-amylases as described in for instance U.S. Pat. No. 4,285, 975 or U.S. Pat. No. 5,180,669. Also proteases are used to increase the amount of freely available nitrogen in the wort to improve fermentation.

Apart from starch other polysaccharides are present in cereal grains as for example β-glucans (Henry, R. J. et al. J. Sci. Food Agric. 36, 1243–1253, 1985). The β-glucanases present in malt are not sufficiently thermostable to be active during the brewing process. These β-glucans are highly viscous and give wort and beer filtration problems. This is the reason why microbial β-glucanases are widely used in the brewing process.

Non-starch polysaccharides also include pentosans, the structure of which has been widely studied recently (Gruppen, H. et al. Carbohydr. Res. 233, 45–64, 1992), in particular those of barley and malt (Vietor, R. J. et al. Carbohydr. Res. 254, 245–255, 1994). A pentosanase from *Penicillium emersonii* has been said to improve the production and extraction of fermentable sugars in brewing (GB 2,150,933).

The use of xylanase B to improve wort quality has also been mentioned in WO94/14965.

Despite the advance which has been made in this area, there is still a need for methods of beer brewing with enzyme preparations for use therein.

SUMMARY OF THE INVENTION

The present invention discloses a process for the production of alcoholic beverages, such as beer, to which a mixture of enzymes is added, which mixture comprises at least an endo-β(1,4)-xylanase, an arabinofuranosidase, an alpha-amylase, an endo-protease and a β-(1,3;1,4)-glucanase, optionally also containing a saccharifying amylase and/or an exo-peptidase. Preferably the enzymes that are necessary for the beer production process are provided by transgenic seeds.

The present invention further discloses transgenic seeds expressing the enzymes necessary in the beer production process.

DESCRIPTION OF THE INVENTION

We have now surprisingly found that the brewing process can be performed in the presence of the mixture of enzymes as claimed, with a minimal amount of malt. This process has been performed to manufacture a classical malt beer, but it can equally well be performed in any process where malt is used to provide enzyme activities.

The enzymes to be used are selected from the group of enzymes which are necessary in the brewing process. They include enzymes which are selected from the group of amylolytic enzymes, from the group of cellulolytic enzymes, from the group of hemicellulolytic enzymes and from the group of proteolytic enzymes.

Amylolytic enzymes comprise enzymes like alpha-amylase, saccharifying amylase, amyloglucosidase, exo-amylase, pullulanase.

Cellulolytic enzymes comprise enzymes like β-1,4-endoglucanase, cellobiohydrolase, β-glucosidase.

Hemicellulolytic enzymes comprise enzymes like β-1,3-1,4-glucanase, xylanase, endo-arabinanase, arabinofuranosidase, arabinoxylanase, arabinogalactanase, ferulic acid esterase.

Proteolytic enzymes comprise enzymes like exopeptidases and endopeptidases (also called prote(in)ases).

In this respect, the choice for a specific amylolytic, cellulolytic, hemicellulolytic or proteolytic enzyme is not critical for the present invention, except that the choice of the enzyme should be such that the properties of the enzyme (such as pH and temperature range) are compatible with the specific circumstances in the brewing process.

Numerous genes encoding amylolytic, cellulolytic, hemicellulolytic and proteolytic enzymes are available to the skilled person. The genes encoding the enzymes of interest can be obtained from any source, plant, animal or microbial. Preferably, the genes are obtainable from a microbial source.

The endo-β-(1,4)-xylanase can be obtained from a culture of *Aspergillus niger* (EP 0 463 706). Arabinofuranosidase is available as isoenzyme A or isoenzyme B (EP 0 506 190) or arabinoxylanhydrolase (EP 0 730 653) from a culture of *Aspergillus niger*. The thermostable amylase is derivable from *Bacillus licheniformis* (WO91/14772, WO92/05259), and is, for example, commercially available under the tradename Brewers Amyliq Thermostable (B.A.T.S.). Activity of the thermostable amylase is expressed in TAU units. The endoprotease can be derived from *Bacillus amyloliguefaciens*, and is also commercially available under the tradename Brewers protease (+) and its activity is expressed in PC units. From the same bacterium also the β-(1,3;1,4)-glucanase can be derived (Hofemeister et al., Gene 49, 177, 1986), which is also commercially available under the tradename Filtrase L 3000 (+). Activity of the glucanase is expressed in BGLU units. The optional saccharifying amylase can also be obtained from commercially available sources (amylase from Aspergillus oryzae under the tradename Brewers Fermex for which the activity is expressed in FAU units), but it can also be obtained from a pure culture of *Penicillium emersonii* (available at the ATCC (American Type Culture Collection) under number ATCC16479). The optional exopeptidase can be derived from a pure culture of *Aspergillus sojae*, as has been deposited at the Centraal Bureau for Schimmelcultures (CBS), Oosterstraat 1, Baarn, The Netherlands, under number CBS 209.96 (*A. sojae* (DS 8351) at Feb. 12, 1996).

The enzyme activities which are currently known to be necessary for beer production are alpha- and β-amylase to convert the starch of the endosperm to fermentable sugars, protease to degrade protein into soluble nitrogen compounds which function as yeast nutrients, and β-glucanase and xylanase to hydrolyze barley β-1,3-1,4-glucans and xylans, respectively, to oligosaccharides which results in a reduction of viscosity and an improvement of filterability. Thus, to provide all necessary enzymes from an exogenous source, i.e. a microbial source, addition of at least 5 different enzymes would be required. Although one micro-organism may be used for the production of all enzymes, different fermentation conditions will be required for optimal production of all enzymes.

By using enzymes from microbial sources, some of the disadvantages of the malting process which have been mentioned before, can be overcome. However, the use of microorganisms as a source of enzymes also has its disadvantages:

a series of different fermentations of at least one microorganism is required to obtain each enzyme in a sufficient amount, the enzyme preparations may contain undesirable side activities, consumers do not flavor additions other than plant material, water and yeast, limited stability of an enzyme preparation during storage at room temperature.

The general use of transgenic seeds containing an enhanced amount of enzyme in industrial enzyme-catalyzed processes is described in international patent application WO91/14772. The direct use of the enzyme-containing seed in an industrial process circumvents the need for first extracting and/or isolating the enzyme. The seed can function as a stable and manageable storage form of enzymes.

For one single enzyme, β-1,3-1,4-glucanase, the expression in barley seeds has been mentioned as an alternative for exogenous addition.

East-German patent application DD 275704 discloses the construction of an expression vector to enable the seed-specific expression of a Bacillus β-1,3-1,4-glucanase in barley. However, at that time effective transformation of barley was not yet known. Using the seeds expressing the Bacillus β-glucanase, a higher amount of grain can substitute for malt without obtaining serious filtration problems. However, other enzyme activities which are necessary in the beer brewing process still have to be obtained from malt or supplemented exogenously.

Mannonen et al. (1993) suggest the incorporation of a fungal β-1,3-1,4-glucanase in barley seeds. In this way, the brewing process would be improved by the expression in the seed of a β-1,3-1,4-glucanase which has a higher thermostability than the endogenous barley enzyme. In this case, however, the intention is to take the seed through the normal malting process. Moreover, also in this case other enzyme activities which are necessary in the beer brewing process still have to be obtained from malt or supplemented exogenously.

In a preferred process of the present invention, the enzymes which are necessary in the brewing process are expressed in transgenic seeds. The thus-produced transgenic seeds expressing said necessary enzymes are in turn used in the beer brewing process. In this way, the use of malt is reduced, whereas the addition of exogenous microbial enzymes is circumvented.

The transgenic seeds expressing the enzymes which are necessary in the beer brewing process are covered by the general name MaltSeed.

Plant genera which are capable of producing the enzyme of interest in their seeds include the species of which the grains or products from grains have a history of use in beer brewing. However, also plant species which are not commonly used for beer brewing may be used as a source of transgenic seed expressing an enzyme of interest, especially in those cases that only a minor amount of said transgenic seed is added to the brewing process. Plant genera which qualify these criteria are, for instance, barley, corn, rice, wheat, sorghum, millet, oats, cassava and the like.

The gene encoding an enzyme of interest is expressed in the plant seed using regulatory sequences functional in a plant or plant seed. Those regulatory sequences include promoter sequences, terminator sequences and, optionally, transcription enhancer sequences.

Promoter sequences may be used which lead to constitutive expression of the gene in the whole plant. Otherwise, promoter sequences may be used which are active in directing expression of the gene to the plant seed.

Furthermore, the expression of an enzyme of interest can be directed either to a specific cellular compartment, such as cytosol, endoplasmatic reticulum, vacuole, protein body, or to the extracellular space, using specific targeting sequences.

The choice for a specific cellular compartment or for the extracellular space depends on the properties of the enzyme of interest and should be made in such a way that an optimal environment for the enzyme is created. For instance, the enzyme of interest should be in an environment that allows optimal stability of the protein during seed maturation. In addition, the enzyme of interest should be in an environment where expression of the enzyme does not inhibit essential plant metabolic processes or lead to a deleterious effect on the plant or seed viability.

In order to be capable of being expressed in a plant cell a DNA sequence coding for the enzyme of choice will usually be provided with regulatory elements enabling it to be recognized by the biochemical machinery of the host and allowing for the open reading frame to be transcribed and translated in the host. It will usually comprise a transcriptional initiation region which may be suitably derived from any gene capable of being expressed in the plant cell, as well as a translational initiation region for ribosome recognition and attachment. In eukaryotic plant cells, such an expression cassette usually comprises in addition a transcriptional termination region located downstream of said open reading frame, allowing transcription to terminate and polyadenylation of the primary transcript to occur. In addition, the codon usage may be adapted to accepted codon usage of the host plant of choice. The principles governing the expression of a DNA construct in a plant cell are commonly understood by those of ordinary skill in the art and the construction of expressible chimeric DNA constructs is now routine.

A special type of replicon is one capable of transferring itself, or a part thereof, to another host cell, such as a plant cell, thereby co-transferring the open reading frame coding for the enzyme(s) according to the invention to said plant cell. Replicons with such capability are herein referred to as vectors. An example of such a vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940,838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host as is for instance the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention those cells will produce the enzymes. Although the principles which govern transcription of DNA in plant cells are not always understood, the creation of chimeric DNA capable of being expressed is now routine. Transcription initiation regions routinely in use for expression of the transformed polynucleotide in a constitutive way are promoters obtainable from the cauliflower mosaic virus, notably the 35S RNA and 19S RNA transcript promoters and the so-called T-DNA promoters of *Agrobacterium tumefaciens*. In particular to be mentioned are the nopaline synthase promoter, octopine synthase promoter (as disclosed in EP 0 122 791 B1) and the mannopine synthase promoter. In addition plant promoters may be used, which may be substantially constitutive, such as the rice actin gene promoter. For seed-specific expression, a gene of cDNA of interest can be inserted behind promoters originating from genes which are specifically expressed in the plant seed. These promoters include promoters of genes encoding seed storage proteins, such as the *Brassica napus* cruciferin promoter, the *Phaseolus vulgaris* phaseolin promoter, the glutelin promoter from Oryza sativa, the zein promoter of Zea mays and the hordein promoter of *Hordeurn vulgare*.

It is further known that duplication of certain elements, so-called enhancers, may considerably enhance the expression level of the DNA under its regime (vide for instance: Kay R. et al. (1987), Science 236, 1299–1302: the duplication of the sequence between −343 and −90 of the CaMV 35S promoter increases the activity of that promoter). In addition to the constitutive 35S promoter, singly or doubly enhanced, examples of high-level promoters are the light-inducible ribulose bisphosphate carboxylase small subunit (rbcSSU) promoter and the chlorophyll a/b binding protein (Cab) promoter. Also envisaged by the present invention are hybrid promoters, which comprise elements of different promoter regions physically linked. A well known example thereof is the so-called CaMV enhanced mannopine synthase promoter (U.S. Pat. No. 5,106,739), which comprises elements of the mannopine synthase promoter linked to the CaMV enhancer.

Specifically with monocot transformation the use of introns between promoter and selectable marker gene enhances expression.

The term "promoter" thus refers to a region of DNA upstream from the structural gene and involved in recognition and binding RNA polymerase and other proteins to initiate transcription. A "plant promoter" is a promoter capable of initiating transcription in plant cells. A "constitutive promoter" is a promoter which is active under most environmental conditions and states of development or cell differentiation.

As regards the necessity of a transcriptional terminator region, it is generally believed that such a region enhances the reliability as well as the efficiency of transcription in plant cells. Use thereof is therefore strongly preferred in the context of the present invention.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimeric DNA according to the invention into a suitable ancestor cell. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses, in planta *Agrobacterium Cumefaciens* mediated gene transfer by infiltration of adult plants or transformation of mature pollen or microspores (EP 0 301 316) and the like. A preferred method according to the invention comprises Agrobacterium-mediated DNA transfer. Especially preferred is the use of the so-called binary vector technology as disclosed in EP A 120 516 and U.S. Pat. No. 4,940,838).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or (tissue) electroporation (Shimamoto, et al, 1989, Nature 338, 274–276). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting embryogenic callus for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J, Michael D, Hasegawa O, Ulian E C, Peterson G, Smith R H, (1991) Plant. Physiol. 95, 426–434).

For barley a preferred transformation method has been described in Tingay, S. et al. (The Plant J. 11(6), 1369–1376, 1997).

To obtain transgenic plants capable of constitutively expressing more than one chimeric gene, a number of alternatives are available including the following:

A. The use of DNA, e.g a T-DNA on a binary plasmid, with a number of modified genes physically coupled to a second selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.

E. Combinations of the above mentioned strategies.

The actual strategy may depend on several considerations such as the purpose of the parental lines (direct growing, use in a breeding programme, use to produce hybrids) but is not critical with respect to the described invention.

It is known that practically all plants can be regenerated from cultured cells or tissues. The means for regeneration vary from species to species of plants, but generally a suspension of transformed protoplasts or a petri plate containing transformed explants is first provided. Shoots may be induced directly, or indirectly from callus via organogenesis or embryogenesis and subsequently rooted. Next to the selectable marker, the culture media will generally contain various amino acids and hormones, such as auxins and cytokinins. It is also advantageous to add glutamic acid and proline to the medium. Efficient regeneration will depend on the medium, on the genotype and on the history of the culture. If these three variables are controlled regeneration is usually reproducable and repeatable.

After stable incorporation of the transformed gene sequences into the transgenic plants, the traits conferred by them can be transferred to other plants by sexual crossing. Any of a number of standard breeding techniques can be used, depending upon the species to be crossed.

In one embodiment of the present invention, transgenic seeds are used which are engineered in such a way that these produce one individual enzyme, allowing for the flexible production of enzyme mixtures with every enzyme activity ratio which is desired. In another embodiment, more than one enzyme activity may be contained in the seeds of an individual transgenic plant line.

The transgenic seeds containing the enzymes of interest can he added together at a desired stage of the brewing process. Alternatively, transgenic seeds containing an enzyme of interest can be added individually, each at a desired point of the process.

The process of the present invention enables the development of a malt with a high level of flavor and color, without having to deal with the enzyme activity of the malt. In the process of the present invention the use of malt is largely bypassed. only a minor amount of malt may still be necessary to provide the beer with flavor and color.

The transgenic seeds containing the desired enzymes can be applied in the most optimal ratio with the grain and, optionally, with a sufficient amount of malt for flavor and color. The transgenic seeds can be mixed beforehand with the grain and the malt. Alternatively, each compound, grain, transgenic seed and malt, can be added at separate stages of the beer brewing process.

Preferably, the individual compounds, transgenic seeds, grain and malt, or the mixture of transgenic seed, grain and malt are milled before addition to the brewing process.

The transgenic seed contains the desired enzymes at an average level that ranges from 0.001–2.5%, preferably from 0.01–1.0%, more preferably from 0.05–0.25% by weight of the seed. Depending on the level of expression in the seed only part or the total of the seeds normally used in the brewing process can be replaced by transgenic seeds. When high levels of expression are reached it is also possible to add the transgenic seeds of other plant genera not normally used in the brewing process without changing too much to the brewing mix.

In the case of malt, preferably part of the malt has received a special treatment, as compared to traditional malt, wherein the malt has been heated during kilning to maximize production of color and flavor compounds. The remaining enzyme activity is negligible after this treatment.

Expression of enzymes in seed as is disclosed in the present invention provides the possibility to circumvent the addition of exogenous microbial enzymes to the brewing process. The costs of the production of transgenic seeds, containing the enzymes are much lower than the costs of the production of enzymes by fermentative processes. Furthermore, transgenic seeds are more conveniently used, since they provide a stable and manageable storage form of enzymes and are easy to handle. The cost reduction and the convenience of use which are coupled with the use of transgenic seeds are especially relevant in the process of the present invention, because the need is circumvented to apply several different enzymes from several microbial fermentations in the beer brewing process.

The course of the process of the present invention is much more predictable than the course of a process using malt as a source of enzymes, since the transgenic seeds contain no other enzyme activities at high levels than those expressed by way of the introduced genes. In addition, the course of the process of the present invention is much more predictable than the course of a process using microbial enzymes, since microbial enzyme preparations display undefined and varying levels of side activities.

One of the areas in which it can be especially used is in African countries where malt importation is banned. The enzymes in that case could be expressed in sorghum, which then could be added to the brewing process.

Next to the applications in the brewing of alcoholic beverages also other applications can be foreseen, in which MaltSeed can replace malted grains.

Malted barley and/or malted wheat are used by millers to standardize the diastasic power of flour. Also hemicellulases (such as xylanase) are added to the flour to improve the gas retention capacity of doughs made from the flour. The addition or use of enzymes in flour can be replaced by using MaltSeed, which is very suitable since the enzymes can be added in the form of grains which anyhow are used.

Identically also in the baking process enzymes can be added as a replacement for the malt which is present in many doughs. Enzymes which are improving the baking process are xylanase, amylase, arabinofuranosidase, exopeptidase. Also the glucose oxidase from *Aspergillus niger* can be expressed in seeds for bakery purposes.

EXAMPLE 1

Activity Measurement of Endo-β-1,4-xylanase

Endoxylanase is obtained from a pure culture of *Aspergillus niger* in a sterile tank and medium. The culture medium contains appropriate carbon and nitrogen sources just as mineral salts. The fermentation is carried out at a constant temperature between 30–40° C. and pH is maintained within the range 3–5.

The activity of the enzyme is measured by hydrolysis of xylan from oat spelts suspended (35 g/l) in 1M glycine buffer pH 2.75. The viscosity of this solution is determined by using a capillary viscometer (Ubbelhode type) at 47° C. The time dt needed for the upper meniscus of the liquid to fall down between two reference points is measured within time T. The slope of the plot T versus 1/dt yields an apparent kinetic constant. 1 Lyx unit is the amount of enzyme needed to reach a value of 1 min-1 for that kinetic constant.

EXAMPLE 2

Activity Measurement of Exopeptidase

A production strain of Aspergillus sojae (DS 8351) is cultured. Exopeptidase activity is expressed as Leucine aminopeptidase units (Leu-A): 1 Leu-A is the amount of enzyme needed to produce 1 µmol p-nitroaniline per minute at pH 7.2 and 20° C. from L-leucine-p-nitroaniline. The test is performed as follows: Leucine paranitroanilid (SIGMA) is dissolved in water at a concentration of 9 mM. 1 ml of the solution is mixed with 1.5 ml 0.1M phosphate buffer pH 7.2. At t=0, 0.5 ml enzyme is introduced and left for reaction at 20° C. Fifteen minutes later, 1 ml 1N HCl is added to stop the reaction. A blank is run with 1N HCl being introduced at t=0. Optical density is determined for the blank ($OD_{blank}$) and for the assay (ODassay) at 400 nm. Activity is calculated as follows:

$$A = \frac{(OD_{blank} - OD_{assay})}{9.8 \times 15} \times \frac{4}{0.5} \text{ Leu-A/ml}$$

EXAMPLE 3

Activity Measurement of Arabinofuranosidase

Isoenzyme A or isoenzyme B or arabinoxylanhydrolase have been obtained from a culture of *Aspergillus niger* or *Aspergillus nidulans* strains. Activity of isoenzymes A and B is measured by the hydrolysis of p-nitrophenyl-alpha-L-arabinofuranoside. 1 ARF unit is the amount of enzyme needed to liberate 1 µmol p-nitrophenol per minute under the test conditions described in Gunata Z. et al. (J. Agric. Food Chem. 38, 772, 1989).

EXAMPLE 4

Activity Measurement of Saccharifying Amylase

Saccharifying amylase is obtained from a pure culture of *Penicillium emersonii* in a sterile tank and medium, which contains appropriate carbon and nitrogen source just as mineral salts. The tank is fed with maltodextrines 10–30 hours (preferably 24 h) after the start of the fermentation. Temperature is maintained in the range of 40–50° C. (preferably 45° C.) and pH is maintained in the range 4.5–5.5 (preferably 5.0). The fermentation is stopped 40–55 h (preferably 48 h) after start.

Saccharifying amylase activity is measured according to the BETAMYL test, commercially available from MEGAZYME, Ireland. 1 BTU is the amount of enzyme needed to produce 1 μmol p-nitrophenol at pH 6.2 and 40° C. from Megazyme's commercial substrate.

EXAMPLE 5

Preparation of Wort Using Microbial Enzymes

A wort was prepared from crude barley grains, variety PLAISANT. Barley was ground with the EBC MIAG mill in order to reach filter press type granulometry. 57 g of the obtained milled barley was suspended in 300 ml warm water (50° C.) and containing:
650 Lyx units endo-β-(1,4)-xylanase
850 ARF units arabinofuranosidase
18 mg B.A.T.S. (thermostable amylase)
6 mg Brewers Protease (+) (endo-protease)
1 mg Filtrase L3000 (+) (β-(1,3;1,4)-glucanase)

The temperature was maintained at 50° C. for 30 minutes and then raised up to 63° C. (rate 1° C./min); the temperature was further maintained at 63° C. for 30 minutes and then raised up to 72° C. (rate 1° C./min) and maintained at that temperature for 30 minutes. It was finally heated up to 76° C. (rate 1° C./min) and maintained at that temperature for 5 minutes. Water was added to compensate for water evaporation. The mash was then poured into a funnel containing Schleicher and Schull paper filter. From the density of the filtered wort, yield was determined as done in any brewery; also viscosity and free amino acids (FAA) levels were determined according to standard EBC procedures.

The yield was 71.5%, viscosity was 2.52 mpa.s and 66 mg/l of free amino acids were measured.

EXAMPLE 6

Comparison of Saccharifying Amylases

A wart was prepared from crude barley grains, variety PLAISANT. Barley was ground with the EBC MIAG mill in order to reach filter press type granulometry. 57 g of the obtained milled barley was suspended in 300 ml warm water (50° C.) and containing:
650 Lyx units endo-β-(1,4)-xylanase
850 ARF units arabinofuranosidase
18 mg B.A.T.S. (thermostable amylase)
6 mg Brewers Protease (+) (endo-protease)
100 Leu-A units exopeptidase
1 mg Filtrase L3000 (+) (E-(1,3;1,4)-glucanase)

According to Table 1 saccharifying enzymes were added to the brew mixture.

TABLE 1

Doses of saccharifying enzymes

| Brew no. | Saccharifying enzyme | |
|---|---|---|
| 1 | none | 0 |
| 2 | Brewers Fermex | 510 FAU |
| 3 | Amylase from *P. emersonii* | 10 BTU |
| 4 | Brewers Fermex + amylase from *P. emersonii* | 510 FAU + 10 BTU |

The temperature was maintained at 50° C. for 30 minutes and then raised up to 63° C. (rate 1° C./min); the temperature was further maintained at 63° C. for 30 minutes and then raised up to 72° C. (rate 1° C./min) and maintained at that temperature for 30 minutes. It was finally heated up to 76° C. (rate 1° C./min) and maintained at that temperature for 5 minutes. Water was added to compensate for water evaporation. The mash was then poured into a funnel containing Schleicher and Schull paper filter. From the density of the filtered wort, yield was determined as done in any brewery; also viscosity and free amino acids (FAA) levels were determined according to standard EBC procedures.

Results of the measured yield, viscosity and FAA given in Table 2 show the effects of the saccharifying enzyme of *Penicillium emersonii* as a substitute of Brewers Fermex whereas no real synergism can be expected from the use of both enzymes. Particularly surprising is the quite positive effect of the amylase of *Penicillium emersonii* on FAA increase and viscosity reduction.

TABLE 2

| | Results | | |
|---|---|---|---|
| Brew no. | Yield (%) | Viscosity (mPa.s) | FAA (12 Plato) (mg/l) |
| 1 | 71.2 | 3.12 | 116 |
| 2 | 74.6 | 2.73 | 114 |
| 3 | 78.2 | 1.99 | 153 |
| 4 | 79.6 | 1.99 | 152 |

EXAMPLE 7

Construction of a Binary Vector Containing a Seed-specific Expression Cassette

An expression construct is constructed in such a way that seed-specific expression is obtained, using sequences of *Oryza sativa L.* glutelin storage protein (Zheng et al., Plant Physiol (1995) 109; 77–786). These sequences may be replaced by those from similar seed-specific genes to achieve the same goal as is the objective of this invention.

For the construction of the expression construct for seed-specific expression, the promoter and terminator sequences from the glutelin (Gt1) gene of *Oryza sativa L.* are synthesized using PCR technology with the genomic clone Ct1 (Okita et al., J. Biol. Chem. 264, 12573–12581,1989) as a template. This gene shows seed-specific expression and its coding and flanking sequences have been determined (EMBL, Genbank Nucleotide Sequence Database accession number D00584)). Two sets of oligonucleotides are synthesized. One to allow amplification of a 2.4 Kb fragment containing the Gt1 5' flanking region encoding as an XhoI/SphI fragment:

5'Gt1.1 5'  GCACAATTCTCGAGGAGACCG  3'  (SEQ ID NO:6)

5'Gt1.2 5'  ATGGATGGCATGCTGTTGTAG  3'  (SEQ ID NO:5)

The other amplification of the 3' flanking sequences as a BamHI/EcoRI fragment (725 bp):

3'Gt1.3 5'  CCTCTTAAGGATCCAATGCGG  3'  (SEQ ID NO:7)

3'Gt1.4 5'  CTTATCTGAATTCGGAAGCTC  3'  (SEQ ID NO:8)

The oligos are designed to contain suitable restriction sites at their termini to allow direct assembly of the expression construct after digestion of the fragments with restriction enzymes. Genes for the enzymes in the mixture according to the invention can be obtained from literature for the endo-xylanase (Mol. Microbiol. 12, 479–490, 1994), for the arabinofuranosidase isoenzyme A and isoenzyme B (EP 0 506 190), for the amylase from *Bacillus licheniformis* (EP 0 449 376), for the protease from *Bacillus amyloliquefaciens*

(J. Bact. 159, 811–819) and for the glucanase form *Bacillus amyloliquefaciens* (Gene 49, 177–187, 1986). The genes for the *saccharifying amylase* from Penicillium and for the exopeptidase from *Aspergillus sojae* can easily be elucidated for a person skilled in the art from the pure enzyme obtainable from the cultures indicated in the description. The codon usage of the genes encoding the enzymes to be expressed in seeds is optimized for expression in monocot seeds. In order to do this the complete gene is made synthetically, a BspHI site is introduced at the ATG start codon and a BamHI site is introduced down-stream of the TAA stop codon both for cloning purposes.

The 2.4 kb PCR product containing the 5' flanking region of Gt1 is digested with XhoI/SphI and cloned in a vector pSLI180 linearized with XhoI/SphI. The resulting vector is linearized with SphI/BamHI and used as a vector in a three-way ligation with the synthetic enzyme-encoding gene and, optionally an oligonucleotide duplex coding for a targeting signal. Targeting can be effectuated to the vacuole, to the apoplast, to the amyloplast or (with e.g. a KDEL-retention signal) to the endoplasmatic reticulum.

From this vector a fragment is isolated, containing the fusions of the Gt1 glutelin promoter, optional signal sequence and the synthetic gene. This fragment is cloned in a three-way ligation with the 725 bp PCR product containing the 3' terminator sequence of Gt1 digested with BamHI/EcoRI into binary vector pMOG22 (in *E. coli* K-12 strain DH5-alpha, deposited at the Centraal Bureau voor Schimmelcultures on Jan. 29, 1990 under accession number CBS 101.90).

EXAMPLE 8

Construction of a Binary Vector Containing the Endo-xylanase Gene in the Seed-specific Expressing Cassette The endoxylanase gene from Aspergillus niger is used to optimise for codon usage in barley. The resulting DNA sequence is depicted in SEQ ID NO:1.

For the expression of the endoxylanase gene extracellular targeting is accomplished by the oligonucleotide duplex grown in a phytotron at 10–20° C. with a 16 hr light period at 10,000–30,000 lux and 50–95% RH. Immature seed are harvested 10–15 days after pollination and sterilized in a bleach solution for 20–40 minutes. Immature embryos are excised from the young caryopses and the embryonic axis is removed with a scalpel blade. The explants are placed scutellum-side up on callus induction medium and incubated at 24° C. in the dark for a period ranging from 16 hours till 7 days.

Embryos are immersed in an Agrobacterium suspension, approximately $0.1–10\times10^9$ bacteria per ml, in which the Agrobacterium contains the constructs comprising the DNA encoding for the enzyme of choice, for 5 to 20 minutes and then transferred to callus induction medium.

Thereupon, embryos are incubated for 2 or 3 days at 24° C. in the dark. After coculture, embryos are transferred to callus induction medium containing antibiotics to kill Agrobacteria, directly combined with a selective agent to start the selection process of transgenic cells. The selection process occurs for up to 8 weeks. Resistant embryogenic callus lines are transferred to regenration medium and incubated in increasing light intensity (500 to 3000 lux) with a 16 hr light period at 24° C. Regenerating plantlets are transferred to hormone free or high cytokinin containing callus induction medium with or without selective agent. After development of a root system, plantlets are transferred to soil and grown to maturity with self-pollination.

EXAMPLE 10

Figure 1:
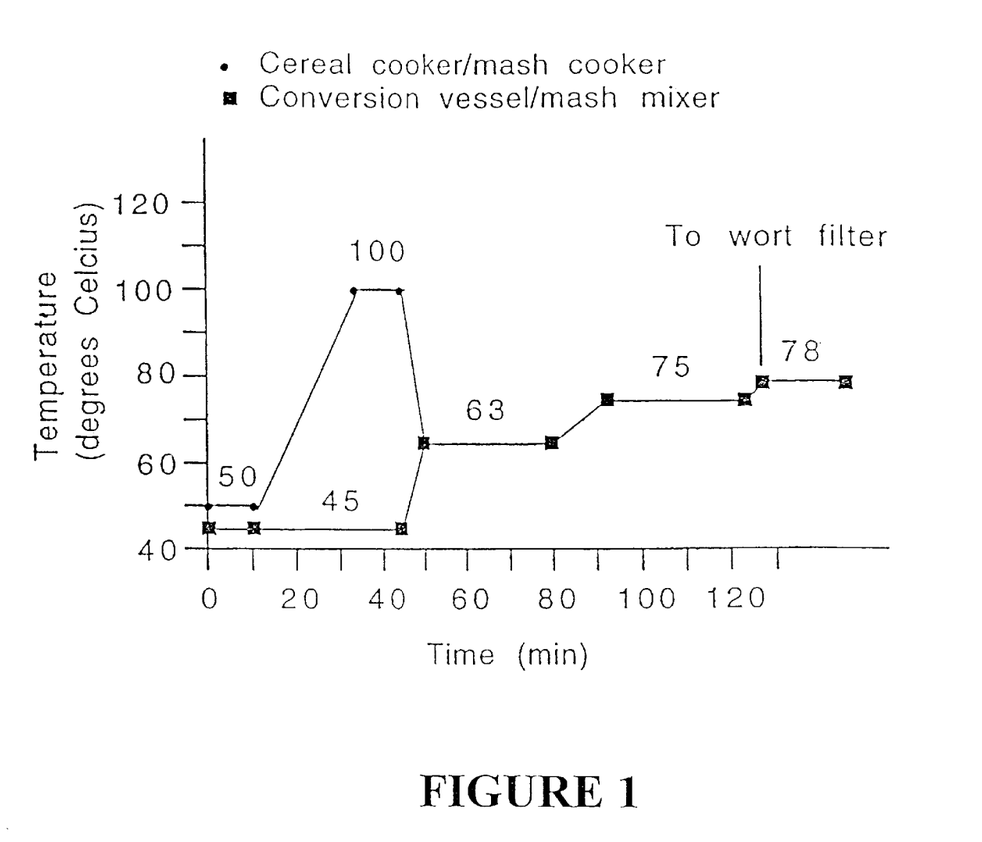
FIG. 1 is a brewing diagram showing conditions used in brewing trials involving test brews prepared according to the invention and a control brew (see Example 10 below)

Three complete pilot brewing trials were performed. Two test brews were done with a severely reduced amount of malt (20% of the raw material) and the control with a normal amount of malt (See Table 3). The two test brews differed in the milling and filtering technology (See Table 3). The brewing diagram for all brews is shown in FIG. 1.

```
                                                                  (SEQ ID NO:3)
PRS.1  5'    AACTTCCTCAAGAGCTTCCCCTTTTATGCCTTCCTTTGTTTTGGCCAATACTTTGTAGCTGTTACGCATGC  3'

(SEQ ID NO:4)
PRS.2  3'GTACTTGAAGGAGTTCTCGAAGGGGAAAATACGGAAGGAAACAAAACCGGTTATGAAACATCGACAATGCGTACGGTACC5'
``` encoding the signal peptide of the tobacco PR-S protein and for the three-way ligation the synthetic xylanase gene digested with BspHI/BamHI is used.

From this vector a 3.1 Kb XhoI/BamHI fragment is isolated, containing the fusions of the Gt1 glutelin promoter, PR-S signal sequence and the synthetic xylanase gene. This fragment is cloned in a three-way ligation with the 725 bp PCR product containing the 3' terminator sequence of Gt1 digested with BamHI/EcoRI into binary vector pMOG22. The resulting vector is designated pMOG1265.

EXAMPLE 9

Barley Transformation

The method used for transformation of immature embryos of *Hordeum vulgare* cv. Golden Promise using *Agrobacterium tumefaciens* is generally as described in Tingay, S. et al., The Plant J. 11(6), 1369–1376, 1997. In short, the protocol is as follows: Donor plants for starting material are

TABLE 3

| Raw material composition, filtering and milling | | | |
|---|---|---|---|
| | Control | Test brew 1 | Test brew 2 |
| Pils malt | 75% | 20% | 20% |
| Maize grits | 25% | 25% | 25% |
| Unmalted barley | — | 55% | 55% |
| Filter | Lautertun | Lautertun | Meura 20001 |
| Milling | Cylinder | Cylinder | Hammer |

From the control mixture 8% malt was used in the cereal cooker together with the maize grits, the other 67% malt was added to the conversion vessel. For the test brews 8% unmalted barley was used in the cereal cooker together with the maize grits, the other 47% unmalted barley was added to the conversion vessel together with the malt.

TABLE 4

Enzymes codes and amounts added per 100 kg raw material

| Enzyme Code | Enzyme | Cereal cooker | Conversion vessel |
|---|---|---|---|
| 1 | Endo-β(1,4)-xylanase | | 117,000 Lyx |
| 2 | Arabinofuranosidase | | 112,500 ARF |
| 3 | B.A.T.S. | 16.5 g | |
| 4 | Brewers Fermex | | 75 g |
| 5 | Brewers protease (+) | | 75 g |
| 6 | Exo-peptidase | | — |
| 7 | Filtrase L3000 (+) | | 23 g |

The enzymes 1, 2, 4, 5 and 7 were added to the conversion vessel, while enzyme 3 was added to the cereal cooker (see Table 4 for enzyme codes and amounts added).

Wort processing results (mashing and lautering) were similar for the test brews and the control. The two test brews did perform similarly in the brewhouse. The test brews gave roughly the same wort, showing that the differences in filtering and milling were not essential. From a taste comparison of the test and control beers it was concluded that all three beers had a quite similar profile. A stronger mouthfeel was observed for the test brews in comparison with the control. This may be due to a higher dextrin level that was found in the analysis of the wort. The amino acid levels in the wort were, although acceptable, lower in the test brews in comparison with the control. The amino acid levels can be increased by addition of the exopeptidase (see example 11). The test brew beers were classified by the tasting panel as good pilsener beers, showing that the partial replacement of malt by the enzyme mixture resulted in a beer that is comparable to a beer manufactured with an amount of malt that is commonly used in the brewing industry.

EXAMPLE 11

Figure 2:
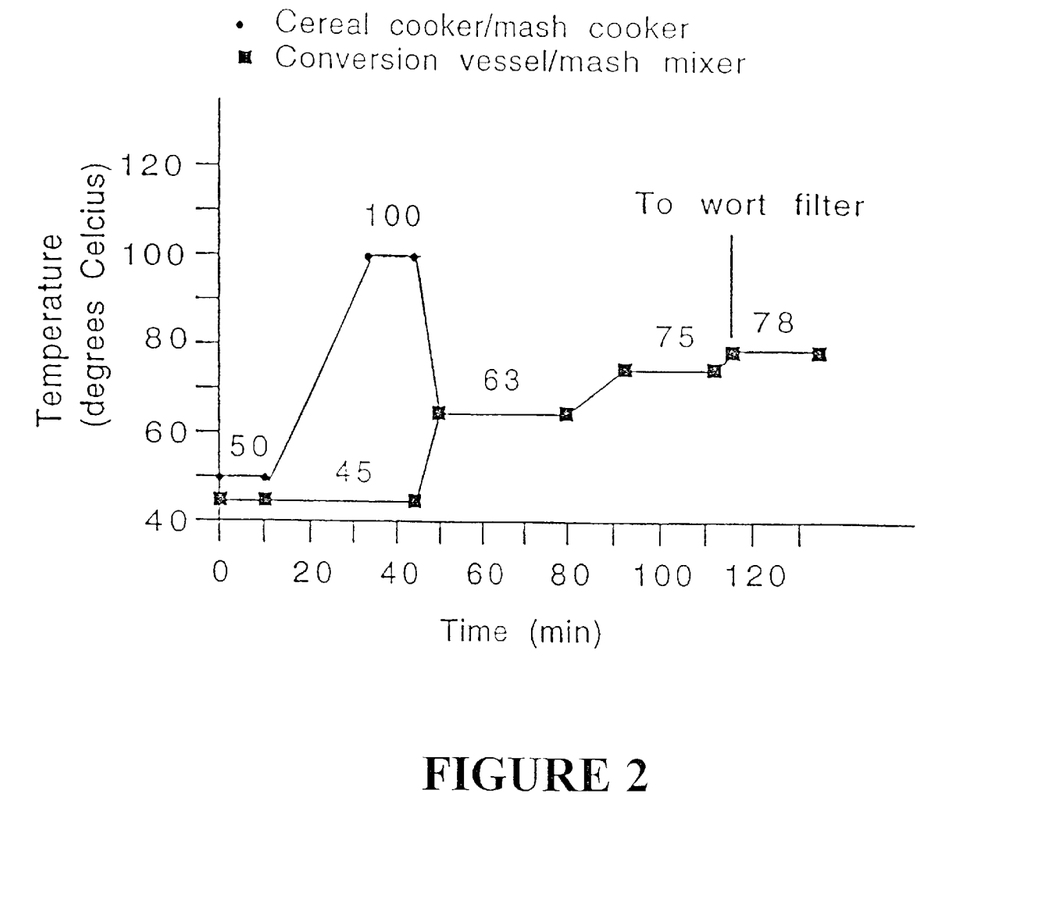
FIG. 2 is a brewing diagram showing conditions used in brewing trials involving a test brew prepared according to the invention and a control brew (see Examples 11 and 12, below).

Two complete pilot brewing trials were performed. The test brew was done with a reduced amount of malt and the control with a normal amount of malt (See Table 5). Filtering was done on the Lautertun. For the brewing diagrams of test brew 1 and the control see FIG. 2.

TABLE 5

Raw material composition

| | Control | Test brew 1 |
|---|---|---|
| Pils malt | 75% | 20% |
| Maize grits | 25% | 25% |
| Unmalted barley | — | 55% |

From the control mixture 8% malt was used in the cereal cooker together with the maize grits, the other 67% malt was added to the conversion vessel. For the test brew 8% unmalted barley was used in the cereal cooker together with the maize grits, the other 47% unmalted barley was added to the conversion vessel together with the malt.

In the test brew, enzymes 1–7 were added to the conversion vessel, while enzyme 3 was added to the contents of the cereal cooker as well (see Table 6 for enzyme codes and amounts of enzyme used).

Wort processing results (mashing and lautering) were similar for the test brews and the control. The free amino acid nitrogen content in the wort was similar for the test brew and the control. The test brew resulted in beer that by tasting was considered to have a quite similar profile as the control. The test brew beer classified by the tasting panel as good pilsener beer, showing that the partial replacement of malt by the enzyme mixture resulted in a beer that is comparable to a beer manufactured with an amount of malt that is in common use in the brewing industry.

TABLE 6

Enzymes codes and amounts added per 100 kg raw material in the test brew

| Enzyme Code | Enzyme | Cereal cooker | Conversion vessel |
|---|---|---|---|
| 1 | Endo-β(1,4)-xylanase | | 117,000 Lyx |
| 2 | Arabinofuranosidase | | 112,500 ARF |
| 3 | B.A.T.S. | 16.5 g | 33.5 g |
| 4 | Brewers Fermex | | 75 g |
| 5 | Brewers protease (+) | | 75 g |
| 6 | Exo-peptidase | | 105,000 LeuA |
| 7 | Filtrase L3000 (+) | | 23 g |

EXAMPLE 12

Transgenic barley grains from seven lines, each expressing one of the enzymes shown in Table 9 are mixed in such amounts that the resulting MaltSeed, when mixed in as 10% of the crude barley, provides enzyme activities as shown in Table 9. The MaltSeed preparation is mixed and ground together with the non-transgenic barley, together constituting 55% of the raw material in the test brew. The raw material compositions in the cereal cooker and the conversion vessel for the test brew are shown in Table B. For the control 8% malt was used in the cereal cooker together with the maize grits. The rest of the raw material was used in the conversion vessel. The distribution of MaltSeed gives the enzyme activities as shown in Table 10 in the conversion vessel and the cereal cooker.

Two brewing trials were performed. The test brew was done with a reduced amount of malt and the control with a normal amount of malt (See Table 7). For the test brew a higher saccharification temperature was used (See Table 7). Filtering was done on the Lautertun. For the brewing diagram of the control and test brew see FIG. 2.

TABLE 7

Composition raw material

| | Control | Test brew 1 |
|---|---|---|
| Pils malt | 75% | 20% |
| Maize grits | 25% | 25% |
| Unmalted barley + MaltSeed | — | 55% |

TABLE 8

Raw material composition per 100 kg total in the test brew

| Raw material | Cereal cooker (kg) | Conversion vessel (kg) |
|---|---|---|
| Malt | | 20 |
| Unmalted barley | 7.2 | 42.3 |
| MaltSeed | 0.8 | 4.7 |
| Maize grits | 25 | |
| Total (kg) | 33 | 67 |

Wort processing results (mashing and lautering) were similar for the test brew and the control. The test brew resulted in beers that by tasting was considered to have a similar profile as the control. The test brew was classified as a classical malt beer by tasting, showing that malt can be (partially) replaced by enzymes provided through transgenic seeds expressing these.

TABLE 9

Amount of enzyme activity added through addition of MaltSeed (units per 100 kg raw material) in test brew 1

| Enzyme Code | Enzyme | Cereal Cooker | Conversion vessel |
|---|---|---|---|
| 1 | Endo-β(1,4)-xylanase | 19,915 Lyx | 117,000 Lyx |
| 2 | Arabinofuranosidase | 19,149 ARF | 112,500 ARF |
| 3 | B.A.T.S. | 107,250 TAU | 630,094 TAU |

TABLE 9-continued

Amount of enzyme activity added through addition of MaltSeed (units per 100 kg raw material) in test brew 1

| Enzyme Code | Enzyme | Cereal Cooker | Conversion vessel |
|---|---|---|---|
| 4 | Brewers Fermex | 57,872 FAU | 340,000 FAU |
| 5 | Brewers protease (+) | 115,745 PC | 680,000 PC |
| 6 | Exo-peptidase | 17,872 Leu-A | 105,000 Leu-A |
| 7 | Filtrase L3000 (+) | 11,701 BGLU | 68,745 BGLU |

What is claimed is:

1. In a process for preparing an alcoholic beverage comprising heating, steeping or mixing a plurality of raw materials to form a brew, the improvement comprising adding to the brew during any stage of its formation a non-malt component or components collectively comprising a mixture of enzymes including at least an endo-β(1,4)-xylanase, an arabinofuranosidase, an alpha-amylase, an endo-protease and a β-(1,3,1,4)-glucanase.

2. A process according to claim 1, wherein said mixture further comprises a saccharifying amylase.

3. A process according to claim 1, wherein said mixture further comprises an exo-peptidase.

4. A process according to claim 2, wherein said mixture further comprises an exo-peptidase.

5. A process according to claim 1, wherein said alcoholic beverage is beer.

6. A process according to claim 2, wherein said alcoholic beverage is beer.

7. A process according to claim 4, wherein said alcoholic beverage is beer.

8. A process according to claim 1, wherein the raw materials consist essentially of malt, grits and unmalted barley, with the malt content of the raw materials being not greater than 20 wt %.

9. A process according to claim 8, wherein the alcoholic beverage has the taste profile of a malt brew made from raw materials having a malt content of about 75 wt %.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 557 base pairs
      (B) TYPE: nucleic acid
      (C) STRANDEDNESS: double
      (D) TOPOLOGY: linear    (ii) MOLECULE TYPE: cDNA    (iii) HYPOTHETICAL: NO    (iv) ANTI-SENSE: NO    (ix) FEATURE:
      (A) NAME/KEY: CDS
      (B) LOCATION: 1..555
      (D) OTHER INFORMATION: /product= "mature protein"

(xi) SEQUENCE DESCRIPTION: SEQ ID NO: 1:

```
ATG AGC GCG GGA ATC AAC TAC GTC CAG AAC TAC AAT GGC AAC CTC GGC      48
Met Ser Ala Gly Ile Asn Tyr Val Gln Asn Tyr Asn Gly Asn Leu Gly
 1               5                  10                  15

GAC TTT ACT TAC GAC GAG TCA GCG GGA ACT TTC AGC ATG TAT TGG GAG      96
Asp Phe Thr Tyr Asp Glu Ser Ala Gly Thr Phe Ser Met Tyr Trp Glu
             20                  25                  30

GAT GGC GTG TCC TCA GAC TTC GTC GTG GGA CTG GGC TGG ACC ACT GGA     144
Asp Gly Val Ser Ser Asp Phe Val Val Gly Leu Gly Trp Thr Thr Gly
         35                  40                  45

TCA TCC AAT GCG ATC ACC TAC AGC GCC GAG TAC TCC GCG TCA GGA TCA     192
Ser Ser Asn Ala Ile Thr Tyr Ser Ala Glu Tyr Ser Ala Ser Gly Ser
     50                  55                  60

GCC TCC TAT CTG GCC GTG TAC GGA TGG GTG AAC TAC CCG CAG GCC GAG     240
Ala Ser Tyr Leu Ala Val Tyr Gly Trp Val Asn Tyr Pro Gln Ala Glu
 65                  70                  75                  80

TAC TAC ATC GTG GAG GAT TAC GGA GAT TAC AAC CCA TGC AGC TCA GCG     288
Tyr Tyr Ile Val Glu Asp Tyr Gly Asp Tyr Asn Pro Cys Ser Ser Ala
                 85                  90                  95

ACC TCC CTC GGA ACT GTG TAC AGC GAC GGC TCC ACC TAC CAG GTC TGC     336
Thr Ser Leu Gly Thr Val Tyr Ser Asp Gly Ser Thr Tyr Gln Val Cys
            100                 105                 110
```

```
ACC GAC ACC CGC ACT AAC GAG CCG TCA ATC ACC GGC ACT TCC ACC TTC      384
Thr Asp Thr Arg Thr Asn Glu Pro Ser Ile Thr Gly Thr Ser Thr Phe
        115                 120                 125

ACC CAG TAC TTC AGC GTG CGC GAG TCC ACT CGC ACC TCA GGA ACC GTG      432
Thr Gln Tyr Phe Ser Val Arg Glu Ser Thr Arg Thr Ser Gly Thr Val
        130                 135                 140

ACC GTC GCG AAC CAC TTC AAC TTC TGG GCG CAG CAC GGA TTC GGC AAC      480
Thr Val Ala Asn His Phe Asn Phe Trp Ala Gln His Gly Phe Gly Asn
145                 150                 155                 160

AGC GAC TTT AAC TAC CAG GTG GTC GCA GTG GAG GCA TGG TCA GGA GCG      528
Ser Asp Phe Asn Tyr Gln Val Val Ala Val Glu Ala Trp Ser Gly Ala
                165                 170                 175

GGC TCA GCG TCC GTC ACT ATC AGC TCC TG                               557
Gly Ser Ala Ser Val Thr Ile Ser Ser
        180                 185
```

(2) INFORMATION FOR SEQ ID NO: 2:

(i) SEQUENCE CHARACTERISTICS:
        (A) LENGTH: 185 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Ser Ala Gly Ile Asn Tyr Val Gln Asn Tyr Asn Gly Asn Leu Gly
1               5                   10                  15

Asp Phe Thr Tyr Asp Glu Ser Ala Gly Thr Phe Ser Met Tyr Trp Glu
                20                  25                  30

Asp Gly Val Ser Ser Asp Phe Val Val Gly Leu Gly Trp Thr Thr Gly
            35                  40                  45

Ser Ser Asn Ala Ile Thr Tyr Ser Ala Glu Tyr Ser Ala Ser Gly Ser
        50                  55                  60

Ala Ser Tyr Leu Ala Val Tyr Gly Trp Val Asn Tyr Pro Gln Ala Glu
65                  70                  75                  80

Tyr Tyr Ile Val Glu Asp Tyr Gly Asp Tyr Asn Pro Cys Ser Ser Ala
                85                  90                  95

Thr Ser Leu Gly Thr Val Tyr Ser Asp Gly Ser Thr Tyr Gln Val Cys
            100                 105                 110

Thr Asp Thr Arg Thr Asn Glu Pro Ser Ile Thr Gly Thr Ser Thr Phe
        115                 120                 125

Thr Gln Tyr Phe Ser Val Arg Glu Ser Thr Arg Thr Ser Gly Thr Val
        130                 135                 140

Thr Val Ala Asn His Phe Asn Phe Trp Ala Gln His Gly Phe Gly Asn
145                 150                 155                 160

Ser Asp Phe Asn Tyr Gln Val Val Ala Val Glu Ala Trp Ser Gly Ala
                165                 170                 175

Gly Ser Ala Ser Val Thr Ile Ser Ser
        180                 185
```

(2) INFORMATION FOR SEQ ID NO: 3:

(i) SEQUENCE CHARACTERISTICS:
        (A) LENGTH: 71 base pairs
        (B) TYPE: nucleic acid
        (C) STRANDEDNESS: single
        (D) TOPOLOGY: linear     (ii) MOLECULE TYPE: cDNA (iii) HYPOTHETICAL: NO (iv) ANTI-SENSE: NO (vi) ORIGINAL SOURCE:
            (A) ORGANISM: Nicotiana tabacum (xi) SEQUENCE DESCRIPTION: SEQ ID NO: 3:

AACTTCCTCA AGAGCTTCCC CTTTTATGCC TTCCTTTGTT TTGGCCAATA CTTTGTAGCT      60

GTTACGCATG C                                                         71

(2) INFORMATION FOR SEQ ID NO: 4:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 4:

CCATGGCATG CGTAACAGCT ACAAAGTATT GGCCAAAACA AAGGAAGGCA TAAAAGGGGA      60

AGCTCTTGAG GAAGTTCATG                                                80

(2) INFORMATION FOR SEQ ID NO: 5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

ATGGATGGCA TGCTGTTGTA G                                              21

(2) INFORMATION FOR SEQ ID NO: 6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

GCACAATTCT CGAGGAGACC G                                              21

(2) INFORMATION FOR SEQ ID NO: 7:

(i) SEQUENCE CHARACTERISTICS:
            (A) LENGTH: 21 base pairs
            (B) TYPE: nucleic acid -continued

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

CCTCTTAAGG ATCCAATGCG G                                              21

(2) INFORMATION FOR SEQ ID NO: 8:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

CTTATCTGAA TTCGGAAGCT C                                              21
```